(12) United States Patent
Gretzer et al.

(10) Patent No.: US 9,744,263 B2
(45) Date of Patent: Aug. 29, 2017

(54) BONE TISSUE IMPLANT COMPRISING STRONTIUM IONS

(75) Inventors: Christina Gretzer, Göteborg (SE); Ingela Petersson, Göteborg (SE)

(73) Assignee: ASTRA TECH AB, Molndal (SE)

( * ) Notice: Subject to any disclaimer, the term of this patent is extended or adjusted under 35 U.S.C. 154(b) by 98 days.

(21) Appl. No.: 13/591,147

(22) Filed: Aug. 21, 2012

(65) Prior Publication Data

US 2012/0316570 A1 Dec. 13, 2012

Related U.S. Application Data

(62) Division of application No. 12/299,010, filed as application No. PCT/EP2008/058859 on Jul. 8, 2008.

(30) Foreign Application Priority Data

Jul. 9, 2007 (EP) .................................... 07112078

(51) Int. Cl.
*A61L 27/30* (2006.01)
*A61C 8/00* (2006.01)
(Continued)

(52) U.S. Cl.
CPC .......... *A61L 27/306* (2013.01); *A61C 8/0009* (2013.01); *A61F 2/30767* (2013.01);
(Continued)

(58) Field of Classification Search
CPC ....................................................... A61F 2/36
(Continued)

(56) References Cited

U.S. PATENT DOCUMENTS 3,919,723 A * 11/1975 Heimke et al. ............ 623/23.57
4,097,935 A 7/1978 Jarcho
(Continued)

FOREIGN PATENT DOCUMENTS

EP 0640353 A2 3/1995
EP 1023910 8/2000
(Continued)

OTHER PUBLICATIONS

Donald Brunette, Titanium in Medicine: Material Science, Surface Science, Engineering, Biological Responses, and Medical Applications, Jan. 2001, Springer Science and Business Media, pp. 609-612.*
(Continued)

*Primary Examiner* — Dah-Wei D Yuan
*Assistant Examiner* — Andrew Bowman
(74) *Attorney, Agent, or Firm* — Birch, Stewart, Kolasch & Birch, LLP

(57) ABSTRACT

The present invention is based on that local administration of strontium ions in bone tissue has been found to improve the bone formation and bone mass upon implantation of a bone tissue implant in said bone tissue. In particular, the invention relates to a bone tissue implant having an implant surface covered by an oxide layer comprising strontium ions and a method for the manufacture thereof. A blasting powder comprising strontium ions, a method for locally increasing bone formation, and the use of strontium ions or a salt thereof for manufacturing a pharmaceutical composition for locally increasing bone formation are also provided by the present invention.

23 Claims, 9 Drawing Sheets

(51) Int. Cl.
A61F 2/30 (2006.01)
A61L 27/06 (2006.01)
A61L 27/50 (2006.01)

(52) U.S. Cl.
CPC ............. A61L 27/06 (2013.01); A61L 27/50 (2013.01); A61F 2002/30677 (2013.01); A61F 2310/00598 (2013.01)

(58) Field of Classification Search
USPC ..... 424/422; 623/20.32, 23.53, 16.11; 3/1.9; 423/598
See application file for complete search history.

(56) References Cited

U.S. PATENT DOCUMENTS

| | | | |
|---|---|---|---|
| 4,365,356 | A | 12/1982 | Broemer et al. |
| 4,737,411 | A | 4/1988 | Graves, Jr. et al. |
| 4,917,702 | A | 4/1990 | Scheicher et al. |
| 5,441,536 | A | 8/1995 | Aoki et al. |
| 5,578,314 | A | 11/1996 | Cochrum et al. |
| 5,705,273 | A | 1/1998 | Denry et al. |
| 6,312,472 | B1 | 11/2001 | Hall et al. |
| 6,527,938 | B2 | 3/2003 | Bales et al. |
| 7,048,541 | B2 | 5/2006 | Hall et al. |
| 7,048,870 | B1 | 5/2006 | Ellingsen et al. |
| 7,105,030 | B2 | 9/2006 | Despres, III et al. |
| 7,291,178 | B2 | 11/2007 | Sul |
| 2003/0183964 | A1 | 10/2003 | Daskalon et al. |
| 2004/0053197 | A1 | 3/2004 | Minevski et al. |
| 2004/0068323 | A1 | 4/2004 | Christensen |
| 2005/0025647 | A1 | 2/2005 | Ortega et al. |
| 2005/0186133 | A1* | 8/2005 | Chen et al. ................. 423/598 |
| 2006/0161256 | A1 | 7/2006 | Ziegler et al. |
| 2006/0286136 | A1* | 12/2006 | Moeggenborg et al. ..... 424/422 |
| 2008/0011613 | A1* | 1/2008 | Wang .......................... 205/318 |
| 2010/0076566 | A1* | 3/2010 | Serafin et al. ............. 623/20.32 |

FOREIGN PATENT DOCUMENTS

| | | |
|---|---|---|
| EP | 1071483 B1 | 1/2001 |
| EP | 1449544 | 8/2004 |
| EP | 1481696 | 12/2004 |
| EP | 1534305 | 6/2005 |
| EP | 1710325 | 10/2006 |
| FR | 2216981 | 9/1974 |
| GB | 1467069 | 3/1977 |
| JP | 2005-95584 A | 4/2005 |
| WO | 94/13334 A1 | 6/1994 |
| WO | 95/17217 A1 | 6/1995 |
| WO | WO-9953971 | 10/1999 |
| WO | WO-0072777 A1 | 12/2000 |
| WO | 01/49327 A2 | 7/2001 |
| WO | WO-02087648 A1 | 11/2002 |
| WO | WO-02/100452 | 12/2002 |
| WO | WO-02096475 | 12/2002 |
| WO | WO-03/039609 | 5/2003 |
| WO | WO-2004008983 A | 1/2004 |
| WO | WO-2004008984 | 2/2004 |
| WO | WO-2004098619 | 11/2004 |
| WO | 2005/084577 A1 | 9/2005 |
| WO | WO-2006004297 | 1/2006 |
| WO | WO-2006004297 A | 1/2006 |

OTHER PUBLICATIONS

Bain, G., et al., "Activated β-catenin induces osteoblast differentiation of C3H10T1/2 cells and participates in BMP2 mediated signal transduction," BBRC, vol. 31, pp. 84-91 (2003).
H. Zreiqat, et al., "Mechanisms of magnesium-stimulated adhesion of osteoablastic cells to commonly used orthopaedic implants," J Biomed Mater Res, vol. 62, pp. 175-184 (2002).
H. Zreiqat, et al., "The effect of surface chemistry modification of titanium alloy on signalling pathways in human osteoblasts," Biomaterials 26, pp. 7579-7586 (2005).
Ni GX, et al., "Strontium-containing hydroxyapatite bioactive bone cement in revision hip arthroplasty," Biomaterials (2006).
S. Sanchez-Salcedo, et al., In vitro Evaluation of Potential Calcium Phosphate Scaffolds for Tissue Engineering, Tissue Engineering, vol. 12, No. 2, pp. 279-290 (2006).
Siebers, M.C., et al., "The influence of the crystallinity of electrostatic spray deposition-derived coatings on osteoblast-like cell behavior, in vitro," J Biomed Mater Res 78A, pp. 258-267 (2006).
Y. Chen, et al., "Synergism between Calcium and Cyclic GMP in Cyclic AMP Response Element-Dependent Transcriptional Regulation Requires Cooperation between CREB and C/EBP-β," Molecular and Cellular Biology, vol. 23, No. 12, pp. 4066-4082 (2003).
Y. Wang, et al., "Osteoblastic cell response on fluoridated hydroxyapatite coatings," Acta Biomater (2006).
Young-Taeg Sul, "The significance of the surface properties of oxidized titanium to the bone response: special emphasis on potential biochemical bonding of oxidized titanium implant," Biomaterials, vol. 24, No. 22, pp. 3893-3907 (2003).
Young-Taeg Sul, et al., "Oxidized, bioactive implants are rapidly and strongly integrated in bone. Part I—experimental implants," Clin. Oral Impl . Res. 17, pp. 521-526 (2006).
Young-Taeg Sul, et al., "The bone response of oxidized bioactive and non-bioactive titanium implants," Biomaterials, vol. 26, No. 33, pp. 6720-6730 (2005).
Young-Taeg Sul, et al., "The electrochemical oxide growth behaviour on titanium in acid and alkaline electrolytes," Medical Engineering & Physics, vol. 23, No. 5, pp. 329-346 (2001).
Ammann, P., "Strontium ranelate: A physiological approach for an improved bone quality," Bone, vol. 38, No. 2, pp. 15-18 (2006).
Baran, D., et al., "Lithium Inhibition of Bone Mineralization and Osteoid Formation," J. Clin. Invest., pp. 1691-1696 (1978).
Bennett, C., et al., "Regulation of osteoblastogenesis and bone mass by Wnt10b," PNAS, vol. 102, No. 9, pp. 3324-3329 (2005).
Bitter K, et al., "Shear bond strengths of different substrates bonded to lithium disilicate ceramics," Dent Mater J. (2006).
Coulombe, J., et al., "In vitro effects of strontium ranelate on the extracellular calcium-sensing receptor," BBRC, vol. 323, No. 4, pp. 1184-1190 (2004).
Krishnan, V., et al., "Regulation of bone mass by Wnt signaling," J. Clin. Invest., vol. 116, No. 5, pp. 1202-1209 (2006).
Li ZY, et al., "Chemical compositions, crystal size and lattice structural changes after incorporation of strontium into biomimetic apatite," Biomaterials (2007).
Mak, Tony, et al., "Effects of Lithium Therapy on Bone Mineral Metabolism: A Two-Year Prospective Longitudinal Study," J. Clin. Endo and Metab, vol. 83, No. 11, pp. 3857-3859 (1998).
Mayer I, et al., "The uptake of lithium ions by synthetic carbonated hydroxyapatite," Calcif tissue Int. (1986).
Medscape, "New drugs for osteoporosis: lasofoxifene and strontium ranelate," Medscape Medical News (2004).
Medscape, "Strontium ranelate for osteoporosis launched in Europe," Medscape Medical News (2004).
Meunier, P., et al., "The Effects of Strontium Ranelate on the Risk of Vertebral Fracture in Women with Postmenopausal Osteoporosis," New England Journal of Medicine, vol. 350, No. 5 (2004).
Ni GX, et al., "Interfacial behaviour of stontium-containing hydroxyapatite cement with cancellous and cortical bone," Biomaterials Oct. 2006.
Nordenstrom, J., et al., "Biochemical Hyperparathyroidism and Bone Mineral Status in Patients Treated Long-Term With Lithium," Metabolism, vol. 43, No. 12, pp. 1563-1567 (1994).
Oliveira, A. L., et al., "Strontium-substituted apatite coating grown on Ti6A14V substrate through biomimetic synthesis," J. Biomed. Mat. (2007).
P. Clement-Lacroix, et al., "Lrp5-independent activation of Wnt signaling by lithium chloride increases bone formation and bone mass in mice," PNAS, vol. 102, No. 48, pp. 17406-17411 (2005).
Ross, F.P., et al., "Nothing but skin and bone," J. Clin. Invest., vol. 116, No. 5, pp. 1140-1149 (2006).

(56) References Cited

OTHER PUBLICATIONS

Xue W, et al., "Osteoprecursor cell response to strontium-containing hydroxyapatite ceramics," J. Biomed Mater Res A. (2006).

Japanese Office Action for Application No. 2010-515495 dated Apr. 16, 2013 (with English translation).

Albrektsson et al., "Osseointegrated Titanium Implants: Requirements for Ensuring a Long-Lasting, Direct Bone-to-Implant Anchorage in Man", Acta Orthop. Scand. vol. 52, 1981, pp. 155-170.

Brånemark et al., "Osseointegrated Implants in the Treatment of the Edentulous Jaw Experience from a 10-year period", The Almqvist & Wiksell Periodical Company, Stockholm, Sweden, pp. 1-132, 1977.

Cooper et al., "Formation of Mineralizing Osteoblast Cultures on Machined, Titanium Oxide Grit-Blasted, and Plasma-Sprayed Titanium Surfaces", The Int'l J. of Oral & Maxillofacial Implants, vol. 14, No. 1, 1999, pp. 37-47.

Esposito, Marco "Titanium for Dental Applications", Springer-Verlag Berlin Heidelberg, pp. 827-873, 2001.

Ni et al., "Strontium-Containing Hydroxyapatite (Sr-HA) Bioactive Cement for Primary Hip Replacement: An In Vivo Study", Wiley InterScience, Published Online Nov. 8, 2005, pp. 409-415.

Sul et al., "Qualitative and quantitative observations of bone tissue reactions to anodised implants", Biomaterials, vol. 23, 2002, pp. 1809-1817.

Sul et al., "Resonance frequency and removal torque analysis of implants with turned and anodized surface oxides", Clin. Oral Impl. Res. vol. 13, pp. 252-259, 2002.

Xiropaidis et al., "Bone-implant contact at calcium phosphate-coated and porous titanium oxide (TiUniteTM)-modified oral implants", Clin. Oral Impl. Res., vol. 16, 2005, pp. 532-539.

European Office Action for Application No. 08774896.8 dated May 26, 2015.

* cited by examiner

US 9,744,263 B2

BONE TISSUE IMPLANT COMPRISING STRONTIUM IONS

This application is a divisional under 35 USC §120 of U.S. application Ser. No. 12/299,010 filed on Oct. 29, 2008, which is the national stage application of International Application No. PCT/EP2008/058859 filed on Jul. 8, 2008, which claims priority under 35 USC §119(a)-(d) of European application No. EP 07112078.6 filed in the EPO on Jul. 9, 2007; the contents of all above-named applications are incorporated herein by reference.

TECHNICAL FIELD

The present invention relates to an implant for implantation into bone tissue and a method for manufacturing thereof.

The invention also relates to a blasting powder and a method for locally increasing bone formation.

TECHNICAL BACKGROUND

A one-stage procedure is nowadays often used for implanting orthopaedic or dental implants, generally metallic implants, into bone tissue.

In the one-stage procedure, a first implant part, such as a dental fixture, is surgically placed into the bone tissue, and a healing cap or a secondary implant part, such as an abutment, is then attached to the first implant part directly after the surgical operation. The soft tissue is thereafter allowed to heal around the healing cap or the secondary implant part. When a healing cap is used, the cap is removed after a few weeks or months without any surgical procedure, and secondary implant parts, such as an abutment and a provisional crown, are attached to the first implant part. The one-stage procedure is for instance described in L. Cooper et al.: "A multicenter 12-month evaluation of single-tooth implants restored 3 weeks after 1-stage surgery," The International Journal of Oral & Maxillofacial Implants, Vol 16, No 2 (2001).

The two-stage procedure, which is another known implantation procedure, involves in a first stage surgically placing a first implant part, such as a dental fixture, into the bone tissue, where it is then allowed to rest unloaded and immobile for a healing period of three months or more in order to allow the bone tissue to grow onto the implant surface to permit the implant to be well attached to the bone tissue, the cut in the soft tissue covering the implant site being allowed to heal over the implant, and in a second stage opening the soft tissue covering the implant and attaching secondary implant parts, such as a dental abutment and/or a restoration tooth, to the first implant part, such as said fixture, forming the final implant structure. This procedure is for instance described by Bråanemark et al.: "Osseointegrated Implants in the Treatment of the Edentulous Jaw, Experience from a 10-year period," Almquist & Wiksell International, Stockholm, Sweden.

However, the fact that the implant not should be loaded during the healing period means that the secondary implant parts may not be attached to the first implant part and/or used during the healing period of three months or more. In view of the discomfort associated with this, it is desirable to minimize the time period necessary for the above-mentioned first stage or even perform the entire implantation procedure in a single operation, i.e. to use the one-stage procedure.

For some patients, it might be considered better to wait at least three months before functionally loading the implant, both for one- and two-stage procedures. However, an alternative using the one-stage procedure is to put the implant in function directly after implantation (immediate loading) or a few weeks after implantation (early loading). These procedures are, for instance, described by D M Esposito, pp. 836-837, in Titanium in Medicine, Material Science, Surface Science, Engineering, Biological Responses and Medical Application, Springer-Verlag (2001).

It is essential that the implant establishes a sufficient stability and bond between implant and bone tissue to enable the above disclosed immediate or early loading of the implant. It shall also be noted that an immediate or early loading of the implant may be beneficial to bone formation.

Some of the metals or alloys, such as titanium, zirconium, hafnium, tantalum, niobium, or alloys thereof, that are used for bone implants are capable of forming a relatively strong bond with the bone tissue, a bond which may be as strong as the bone tissue per se, sometimes even stronger. The most notable example of this kind of metallic implant material is titanium and alloys of titanium whose properties in this respect have been known since about 1950. This bond between the metal and the bone tissue has been termed "osseointegration" (Albrektsson T, Bråanemark P I, Hansson H A, Lindström J, "Osseointegrated titanium implants. Requirements for ensuring a long-lasting, direct bone anchorage in man," Acta Orthop Scand, 52:155-170 (1981)).

It may be noted that in contact with oxygen, titanium, zirconium, hafnium, tantalum, niobium and their alloys are instantaneously covered with a thin oxide layer. This native oxide layer on titanium implants mainly consists of titanium (IV) dioxide ($TiO_2$) with minor amounts of $Ti_2O_3$, $TiO$ and $Ti_3O_4$.

Although the bond between the (oxidised) metal, e.g. titanium, and the bone tissue may be comparatively strong, it is desirable to enhance this bond.

There are to date several methods for treating metallic implants in order to obtain a better attachment of the implant, and thus improved osseointegration. Some of these involve altering the morphology of the implant, for example by creating irregularities on the implant surface in order to increase the surface roughness in comparison to an untreated surface. It is believed that an increased surface roughness, which gives a larger contact and attachment area between the implant and the bone tissue, provides a better mechanical retention and strength between implant and bone. It is well-known within the art that a surface roughness can be provided by, for example, plasma spraying, blasting or acid etching.

Other methods for obtaining a better attachment of the implant to the bone tissue involve alteration of the chemical properties of the implant surface.

Several methods involve the application of a layer of ceramic material, such as hydroxyapatite, to the implant surface, inter alia in order to improve the bonding of the implant to bone since hydroxyapatite is chemically related to bone. A disadvantage with ceramic coatings is, however, that they may be brittle and may flake or break off from the implant surface, which may in turn lead to an ultimate failure of the implant.

Other methods for altering the chemical properties of the implant involve application of fluorine and/or fluoride on the implant surface (WO 94/13334, WO 95/17217, WO 04/008983, and WO 04/008984).

It is known from, for instance, U.S. Pat. No. 4,917,702, U.S. Pat. No. 5,441,536, WO 99/53971, WO 03/039609 and EP 1481696, to incorporate certain ions, such as $Mg^{2+}$, $Ca^{2+}$, $Mn^{2+}$ or $Sr^{2+}$, in calcium phosphate-containing coatings, such as hydroxyapatite, applied on implants in order to promote bone growth onto the implant.

For instance, WO 01/49327 and Ni G X et al., "Strontium-Containing Hydroxyapatite (Sr-HA) Bioactive Cement for Primary Hip Replacement: An In vivo Study," Inc J Biomed Mater Res Part B: Appl Biomater 77B, pp. 409-415 (2006); Ni et al. disclose bioactive bone cements including strontium-containing hydroxyapatite.

Xue W, et al., "Osteoprecursor Cell Response to Strontium-Containing Hydroxyapatite Ceramics," J Biomed Mater Res A, 79(4), pp. 804-814 (2006), shows that Sr-containing hydroxyapatite has a greater ability to induce apatite precipitation than hydroxyapatite and that strontium stimulates osteoprecursor cell (OPC1) differentiation.

In addition, EP 1023910 describes a hydroxylated and hydrophilic implant enclosed in a sealed container comprising, for instance, pure water and divalent cations, such as $Mg^{2+}$, $Mn^{2+}$ or $Sr^{2+}$. These cations are said to adsorb on the oxide layer of the implant.

WO 2006/004297 discloses an osseoinductive metal implant, such as titanium or an alloy thereof, comprising a layer of metal oxide and a layer of a bio-active material composed of any one or more of Li, Na, K, Rb, Cs, Fr, Mg, Ca, Sr, Ba, Ra, Sc, Y, Lu, Ti, Zr, Hf, Nb, Ta, Cr, Mo, W, Mn, Re, Fe, Ru, Os, Co, Rh, Ir, Ni, Pd, Pt, Cu, Ag, Au, Zn, Ga, In, Ti, Sn and Bi formed thereon. Said layer of a bio-active material is formed by implanting the ionized bio-active material into the surface of said metal oxide. A working example is, however, only described for a titanium implant comprising incorporated ionized calcium in its titanium oxide layer.

Mention can also be made of WO 2002/096475 referring to a titanium implant comprising calcium, phosphor or sulphur in the titanium oxide layer, and WO 2005/084577 referring to a titanium implant comprising magnesium in the titanium oxide layer.

Although implants which provide a comparatively strong bond between the implant surface and the bone exist, there is a need in the art to enhance this bond, i.e. to improve the "osseointegration" process of an implant in bone tissue.

Thus, there is a need in the art to provide an implant having a desired rate of attachment and which has the ability to form a mechanically strong bond between the bone and the implant upon implantation thereof in bone tissue.

SUMMARY OF THE INVENTION

It is an object of the invention to meet the above mentioned needs.

Thus, a biocompatible implant intended for implantation into bone tissue is to be provided.

The inventors have found that strontium ions locally administered in bone tissue has a local effect on the bone formation and bone mass in the bone tissue.

It has further been found that an implant comprising a surface oxide layer comprising and/or releasing strontium ions induces an increased production of alkaline phosphatase in osteoblasts, which is crucial for further differentiation and mineralisation. Furthermore an increased production of prostaglandin E2 (PGE2) is observed with the inventive implant. Hence, an improved rate of bone formation and an improved rate of attachment between bone tissue and the implant may be achieved, further improving the possibility of immediate or early loading of the implant.

Furthermore, it has been found that an implant comprising a surface oxide layer comprising and/or releasing strontium ions provides an increased proliferation of osteoblasts and an increased production of osteoprotegerin, in comparison to a metallic implant comprising a surface oxide layer containing, for instance, calcium or magnesium ions. An improved bone mass is thereby provided which implies a mechanically stronger bond between the implant and the bone tissue.

Accordingly, it has been found that locally administered strontium ions improve the osseointegration process of an implant in bone tissue.

According to a first aspect of the invention, the above objects are achieved with an implant for implantation into bone tissue which has a surface covered by an oxide layer, wherein said oxide layer comprises strontium ions.

According to a second aspect of the invention, a method for manufacturing a bone tissue implant having the above mentioned characteristics is provided. The method comprises the steps of:

a) providing an implant having an implant surface;
b) forming an oxide layer covering said implant surface;
c) forming negatively charged ions on said oxide layer; and
d) bringing said oxide layer into contact with strontium ions.

The method of the invention is inexpensive and easy to carry out, thereby enabling mass production. Furthermore, it is easy to sterilize and to store.

According to a third aspect of the present invention, a blasting powder comprising a metal oxide comprising strontium ions is provided.

According to a fourth aspect of the invention, a method for locally increasing bone formation is provided. Said method comprises administering a composition comprising strontium ions or a salt thereof and a pharmaceutically acceptable carrier to a person in need thereof.

A fifth aspect of the invention relates to the use of strontium ions or a salt thereof for manufacturing a pharmaceutical composition for locally increasing bone formation.

A sixth aspect of the invention relates to a kit for implantation of an implant into bone tissue comprising an implant and a composition comprising strontium ions or a salt thereof and a pharmaceutically acceptable carrier.

Other features and advantages of the present invention will become apparent from the following description of the invention.

DETAILED DESCRIPTION OF THE INVENTION

As used herein the term "implant" includes within its scope any device intended to be implanted into the body of a vertebrate animal, in particular a mammal, such as a human. Implants may be used to replace anatomy and/or restore any function of the body.

Generally, an implant is composed of one or several implant parts. For instance, a dental implant usually comprises a dental fixture coupled to secondary implant parts, such as an abutment and/or a restoration tooth. However, any device, such as a dental fixture, intended for implantation may alone be referred to as an implant even if other parts are to be connected thereto.

As used herein the term "implant for implantation into bone tissue" refers to implants intended for at least partial implantation into bone tissue, such as dental implants, e.g. one-piece implants, orthopaedic implants, and the like. An implant for implantation into bone tissue may also be referred to as a bone tissue implant.

As used herein the term "implant surface" refers to at least one defined surface region of an implant. Thus, the defined surface region may include the entire surface area of the implant or portions thereof.

An example of an implant surface intended for implantation into bone tissue is the surface of a dental fixture that is intended for implantation into the jawbone of a patient and to be in contact with bone tissue.

Another example of an implant surface intended for implantation into bone tissue is the surface of a hip joint implant that is intended for implantation into the femur of a patient.

The present invention relates to an implant for implantation into bone tissue having a surface; said surface being covered by an oxide layer, wherein said oxide layer comprises strontium ions.

An implant according to the invention is biocompatible and has a local effect on the bone formation and bone mass in the bone tissue. Furthermore, the inventive implant causes an increased proliferation of osteoblasts, and an increased production of alkaline phosphatase, osteoprotegerin, and prostaglandin E2 in bone tissue.

Alkaline phosphatase is an enzyme produced by osteoblasts which plays a major role in the mineralization of bone, and osteoprotegerin is a cytokine known to increase the bone mineral density and bone volume in the bone tissue. Further, prostaglandin E2 has a positive effect on bone formation and an inhibiting effect on bone resorption. The production of alkaline phosphatase, osteoprotegerin and prostaglandin E2 clearly indicates that the implant according to the invention has a positive effect on bone remodelling.

Figure 12:
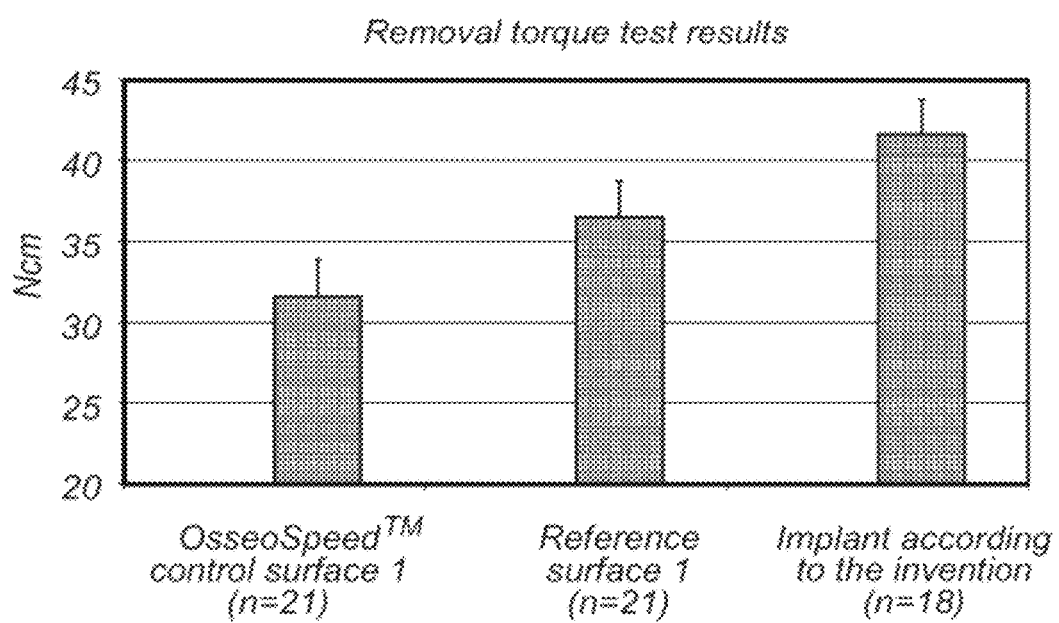
FIG. 12 illustrates the removal torque test (RTQ) values after 6 weeks of implantation in rabbit tibia of an implant comprising strontium according to the invention compared to two control implant surfaces.

An implant according to the invention provides an improved implant stability and bone tissue response as measured by removal torque (RTQ) tests (FIG. 12).

The oxide layer covering the implant surface comprises strontium ions which are dispersed in at least part of the oxide layer.

Strontium is a positively charged, non-toxic ion which has been found to be easily dispersed in the oxide layer covering the surface of the implant.

Furthermore, strontium is known to be a bone-seeking element taken up by bone. For example strontium ranelate, sold under the tradename Protelos by Les Laboratoires Servier, has been used for a few years for treatment of osteoporosis. Studies have shown that oral administration of strontium ranelate both increases bone formation via enhanced osteoblastic cell replication and decreases bone resorption via decreased osteoclastic activity. Thus, improvements in new bone formation and bone mineral density are achieved. Meunier P J, et al., "The Effects of Strontium Ranelate on the Risk of Vertebral Fracture in Women with Postmenopausal Osteoperosis," N Engl J Med, Vol 350, pp 459-468 (2004); Coulombe J, et al., "In Vitro Effects of Strontium Ranelate on the Extracellular Calcium-Sensing Receptor," Biochem and Biophys Res Comm, Vol 323, issue 4, pp 1184-1190 (2004); Ammann P, "Strontium Ranelate: A Physiological Approach for an Improved Bone Quality," Bone, Vol 38, Issue 2, Suppl 1, pp 15-18 (2006); Li Z Y, et al. "Chemical Composition, Crystal Size and Lattice Structural Changes After Incorporation of Strontium into Biomimetic Apatite," Biomaterials, 28(7), pp 1452-1460 (2006).

The fact that strontium previously has been used for the treatment of osteoporosis implies that the toxicological picture and the side effects upon systemic administration are well known. Furthermore, strontium has a relatively simple chemistry and is generally indestructible and unaffected by e.g. sterilization.

The incorporation of strontium ions into the oxide may disrupt the oxide structure, thereby making the oxide more reactive. When the oxide layer is incorporated with positively charged strontium ions, an increased positive surface charge density is provided on the oxide surface (implant surface). Hence, electron rich proteins in the bone tissue may be electrically attracted to the surface. Incorporated ions can also affect the conductivity of the oxide which may have a positive effect on osseointegration and hemocompatibility.

At least part of the oxide layer should comprise strontium ions, and the desired osseoinductive effect of strontium in an implant of the invention may be achieved by the presence of the ions in the oxide layer. However, it may also be achieved by the release of strontium ions from the oxide layer into the physiological fluid surrounding the implant.

Figure 1:
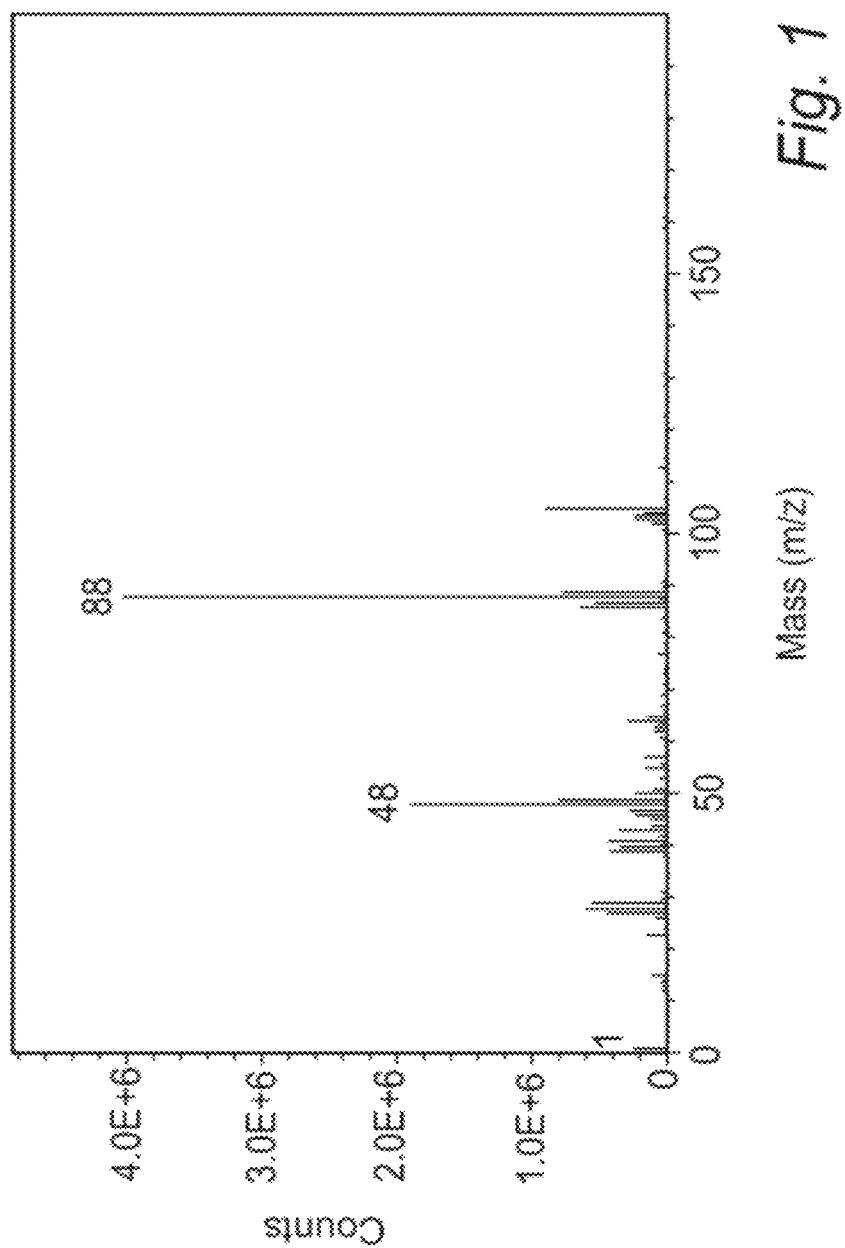
FIG. 1 illustrates the presence of strontium (peak no 88) on a sterilized titanium sample (from TOF-SIMS measurements).
Figure 2:
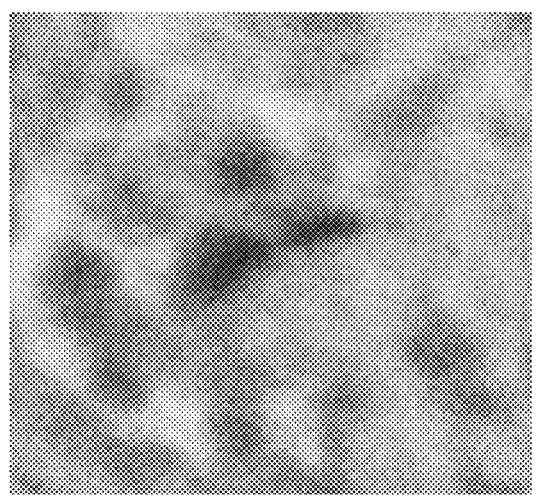
FIG. 2 is a TOF-SIMS image illustrating the presence and the distribution of strontium for a sterilized titanium sample after anodization in $Sr(OH)_2$. (Strontium is shown in white.)

Preferably, the strontium ions are homogenously dispersed in the oxide layer. The homogenous distribution of strontium ions on an implant surface is illustrated in FIG. 2.

The implant according to the present invention is suitably a metallic implant, such as an implant made of titanium or an alloy of titanium.

In embodiments however, the implant can be a non-metallic implant comprising e.g. a ceramic, a plastic or a composite material. In such embodiments, the implant surface is a metallic implant layer applied on the non-metallic implant, whereby a partly metallic implant surface is provided. The metallic implant layer preferably comprises titanium or an alloy of titanium.

However, the metallic implant, and the metallic implant layer are not limited to a specific metal, but may be made of any biocompatible metallic material, such as zirconium or an alloy thereof, hafnium or an alloy thereof, niobium or an alloy thereof, tantalum or an alloy thereof, a chromium-vanadium alloy, or any combination of these materials.

The oxide layer covering the surface of the implant has a thickness within the range of from 2 to 100 nm.

In contact with oxygen, titanium, zirconium, hafnium, tantalum, niobium and their alloys are instantaneously covered with a thin oxide layer. This native oxide layer on titanium implants mainly consists of titanium(IV) dioxide ($TiO_2$) with minor amounts of $Ti_2O_3$, $TiO$ and $Ti_3O_4$.

In preferred embodiments, the oxide layer is an oxide layer which is formed spontaneously, e.g. in contact with air. The thickness of such a spontaneously formed oxide layer is within the range of from 2 to 18 nm, for example within the range of from 2 to 6 nm.

The oxide layer according to the invention does not grow substantially thicker over time and protects the underlying metallic surface from reacting with any surrounding agent.

Metal implants surfaces covered by oxide layers are known in the art. However, several prior art documents stress the importance of providing a thick oxide layer, preferably above 600 nm onto the implant surface (Sul et al., "Resonance frequency and removal torque analysis of implants with turned and anodized surface oxides," Clin. Oral. Impl. Res., Vol 13, pp 252-259 (2002); Sul et al., "Qualitative and quantitative observations of bone tissue reactions to anodised implants," Biomaterials, Vol 23, No 8, pp 1809-1817 (2002)). Such implants require an additional step of oxidation since oxide layers of the above mentioned thickness are not obtainable spontaneously.

The present inventors have found that an oxide layer having a thickness of less than 100 nm, preferably an oxide layer having the thickness of a native oxide layer, i.e. a spontaneously formed oxide layer, of less than 18 nm is more suitable for implantation into bone tissue since thick oxide layers may be very brittle. Furthermore, thick oxide layers may lead to cracking and peeling during longer periods of implantation of an implant in bone tissue.

This finding is in contrast to Xiropaidis et al. who states that titanium implants with native oxide layers are considered less osteoconductive. (Xiropaidis et al., "Bone-implant contact at calcium phosphate-coated and porous titanium oxide (TiUnite™)-modified oral implants," Clin. Oral. Impl. Res, No 16, pp 532-539 (2005)).

An oxide layer according to the invention does not interfere with, or modify the topography of the implant surface. Furthermore, an implant comprising an oxide layer having a thickness of less than 100 nm, e.g. less than 18 nm, e.g. between 2 and 6 nm is biocompatible making it suitable for incorporation into the human body.

Hence, an oxide layer comprising strontium ions according to the invention is suitable for any geometry or any substrate.

The implant surface of the implant according to the invention is preferably a metallic implant surface comprising a metal oxide layer on its surface.

In particular, the implant, in particular the surface of the implant according to the invention comprises titanium or an alloy thereof. Such an implant surface is thus covered by a titanium oxide layer.

Accordingly, in an implant of the present invention, the oxide layer covering the surface of the implant is a metal oxide layer formed on the metallic surface of the implant.

In embodiments, the implant according to the invention may further be provided with a deposit on top of the oxide layer. Such a deposit may comprise a bone stimulating agent, such as strontium, lithium, calcium, magnesium or any other ion having a bone stimulating effect. Typically, the deposit comprises strontium ions.

As used herein the term "deposit" relates to a continuously or discontinuously film provided on top of the oxide layer. Such a deposit may have any thickness and is not incorporated into the oxide layer, but is provided thereon.

Typically, the deposit is a salt precipitation comprising any one or a combination of ions selected from strontium, lithium, magnesium and calcium.

Usually, the deposit is a strontium salt precipitation, i.e. a strontium salt which is precipitated on top of the oxide layer of the implant surface.

Examples of suitable strontium salts are strontium hydroxide, strontium fluoride, strontium chloride, strontium sulphate, strontium nitrate, strontium carbonate. However, any strontium salt capable of being at least partly dissolved in the physiological fluid surrounding the implant may be used. Such salts are known to a person skilled in the art.

Upon implantation, a deposit comprising a salt precipitation dissolves easily and rapidly in the surrounding fluid such that the bone stimulating ions are released from the implant. An implant provided with such a deposit on its surface may be particularly beneficial in situations where an implant needs to integrate more rapidly, e.g. in bone of poor quality and quantity.

An advantage associated with an implant comprising a deposit of the above mentioned kind on its surface is that bone stimulating ions, e.g. strontium ions are easily and efficiently released into the physiological fluid surrounding the implant. Hence, a higher dose of bone stimulating ions, e.g. strontium ions may be released into the surrounding fluid.

Accordingly, the desired effect of strontium may be obtained both from ions present in the oxide in the oxide layer on the implant surface and ions released therefrom.

In embodiments of the implant according to the invention which comprises strontium ions, it has been found advantageous that said implant surface has an average atomic concentration of at least 0.5 at %, for instance measured with X-ray photoelectron spectroscopy (XPS). However, the initially provided amount of strontium might need to be higher due to potential decrease during storage of the implant.

An implant according to the present invention suitably lacks a coating comprising a calcium phosphate compound. As outlined in the introduction, such implants are more prone to flake or break off from the implant surface, which may lead to an ultimate failure of the implant.

In embodiments of the invention, the implant surface may further comprise a micro-roughness having a root-mean-square roughness ($R_q$ and/or $S_q$) of ≤250 nm (i.e. a micro-roughness comprising pores having a pore diameter of ≤1 μm and a pore depth of 500 nm) on at least a part of the implant surface. As used herein the term "nano- or micro-roughness" refers to a surface roughness comprising surface irregularities having dimensions smaller than 1 µm.

Such surface roughness is likely to give a larger contact and attachment area between the implant and the bone tissue, and provide a better mechanical retention and strength between implant and bone.

In alternative embodiments, the implant surface comprises fluorine and/or fluoride, such as 0.2-20 at %, and optionally also a micro-roughness having a root-mean-square roughness ($R_q$ and/or $S_q$) of ≤250 nm, on at least a part of the implant surface.

Optionally, the surface of the implant according to the invention may comprise a macro-roughness. As used herein the term "macro-roughness" refers to a surface roughness comprising surface irregularities having dimensions greater than 1 µm.

It shall also be noted that the implant surface may be either threaded or unthreaded or it may be given other use dependent topographical features.

Furthermore, the present invention relates to a method for manufacturing a bone tissue implant having the characteristics outlined above, comprising the steps of:
a) providing an implant having an implant surface;
b) forming an oxide layer covering said implant surface;
c) forming negatively charged ions on said oxide layer; and
d) bringing said oxide layer into contact with strontium ions.

As previously mentioned, the implant may be a metallic implant, or it may be a non-metallic implant provided with a metallic surface. When non-metallic implants are used in the present invention, a metallic implant surface may be provided by any suitable technique known to those skilled in the art. For example, any suitable electrochemical treatment can be used.

An oxide layer covering the surface of the implant is preferably formed spontaneously, e.g. in contact with air. Such a layer is passive and inert, i.e. it is stable and prevents the underlying metallic surface from further reaction.

It is however possible to use any conventional oxidization techniques in the method above. Hence, the method is not limited to the spontaneous formation of an oxide layer. For instance, an oxide layer can be formed on a metallic implant surface by anodic oxidation of the implant in an electrolyte, such as an aqueous solution of an organic acid. An oxide layer can also be formed on a metallic implant surface by heating in air at, for instance, 150-1300° C. Moreover, an oxide layer can be formed on a metallic implant surface by precipitating the oxide on the implant surface from a suitable solution.

As already mentioned, an oxide layer covering said implant surface is preferably formed spontaneously, which is advantageous as no additional step of oxidation is actually required.

Referring to step c) in the method outlined above, negatively charged ions may be formed on said oxide layer by subjecting the implant surface to an alkaline environment.

In contact with an aqueous solution the metal oxide, e.g. titanium oxide surface will disrupt the water molecule structure in its close vicinity, and, depending on the pH, become either positively or negatively charged. When the surface is uncharged and no ions are adsorbed on the surface, the pH is called the point of zero charge $pH_{PZC}$. The $pH_{pzc}$ for titanium oxide is between 5-7.

Hence, when the titanium oxide surface is surrounded by an aqueous, alkaline environment, e.g. alkaline solution having a pH over 7, the surface becomes slightly negatively charged due to the formation of surface bound, negatively charged hydroxide groups. Positively charged strontium ions, which may be present in a surrounding solution can thus be electrically attracted to the oxide surface (implant surface) and thereby become incorporated into at least part of the oxide layer, typically in the upper part of the oxide layer. Preferably, the strontium ions are homogenously distributed in the oxide layer.

An alkaline environment may be achieved locally on the surface of the oxide; i.e. negatively charged ions may be formed on the oxide layer by applying a potential which is more negative than −0.5 V; typically in the range of from −0.5 to −3.5 V. The application of such a potential will increase the disruption of water molecules, generating the formation of hydrogen gas, and surface bound, negatively charged hydroxide groups on the implant surface.

Alternatively, an alkaline environment is achieved by subjecting the implant surface to an alkaline solution, e.g. by soaking the implant surface in an alkaline solution. Such an alkaline solution should have a pH higher than 7, e.g. higher than 10; and typically higher than 11. The soaking time may be less than 30 minutes, e.g. less than 20 minutes, typically between 10 and 15 minutes.

The implant surface is then brought into contact with positively charged strontium ions; e.g. by subjecting the implant surface to a solution comprising strontium ions. The step of bringing said oxide layer into contact with strontium ions may be performed simultaneously with or after the step of forming negatively charged ions on said oxide layer. Preferably the steps c) and d) of the method according to the invention are performed simultaneously.

For example, by applying a potential within the range of from −0.5 V to −3.5 V in a solution comprising strontium, negatively charged hydroxide groups will be formed, leading to an electrostatic interaction between surface bound hydroxide groups and strontium ions present in the solution. This electrostatic interaction results in that strontium ions are incorporated into the oxide layer. This is further described in Example 1.

The solution comprising strontium ions may be a solution comprising strontium hydroxide in a concentration of 0.03 M, which represents the solubility product of strontium hydroxide, or less. When the concentration of $Sr(OH)_2$ exceeds 0.03 M, salt crystals will be formed and precipitate on the surface of the oxide. In step c) of the method according to the invention, it is desired that the ions become incorporated into the oxide, and hence the concentration of $Sr(OH)_2$ should not exceed the solubility product.

The steps of forming negatively charged ions on the oxide surface and bringing said oxide layer into contact with strontium ions, thereby incorporating strontium ions into the oxide layer covering the surface of the implant is not limited to a specific method but may be achieved by any suitable method, or any combination of methods. For example, the implant surface may be anodized in an alkaline solution comprising strontium ions. Example 1 illustrates the incorporation of strontium ions by anodizing in strontium hydroxide.

By subjecting the implant surface to an anodization step, the thickness of the oxide layer will be affected. However, as the anodizing is preferably performed with a relatively low scan rate, e.g. below 6 mV/s until reaching 8V, the thickness of the oxide will not grow thicker than 100 nm.

Hence, strontium ions are incorporated into the oxide layer by means of the electrostatic interaction between negatively charged hydroxide groups formed on the implant surface and positively charged strontium ions present in a surrounding solution.

Optionally, the method according to the invention may comprise the step of rinsing and/or cleaning said implant surface after step d). Furthermore, the implant surface may be dried and sterilized after said rinsing step.

In embodiments, the method according to the invention further comprises the step of forming a deposit comprising a bone stimulating agent such as strontium, lithium, calcium, magnesium on top of said oxide layer, e.g. by precipitating a salt comprising the above mentioned ions on the surface of the implant; i.e. on the oxide layer covering said surface.

The salt may be any suitable salt of the ions above which is at least partly soluble in the physiological fluid surrounding the implant. The precipitation of a salt on the implant surface will form a continuous or a non-continuous film on the surface. The thickness of the deposit will depend on the amount of salt precipitated.

Such a salt deposit dissolves easily and rapidly in contact with the physiological fluid surrounding the implant such that the desired bone stimulating effect is achieved by the release of bone stimulating ions from the implant surface.

When the deposit is a strontium salt precipitation, the step of forming such a deposit may be achieved by modifying the above described methods for forming negatively charged ions on the surface of the oxide layer. For example, a potential more negative than −3.5 V can be applied. Such a negative potential gives rise to a significantly enhanced hydrogen gas development and an increased disruption of water molecules. Hence, an excess of negatively charged, surface bound hydroxide groups are formed at the oxide surface resulting in a deposit, i.e. a precipitate of strontium hydroxide on top of the oxide layer. See example 2 for further description.

Furthermore, by subjecting the implant surface to a solution comprising strontium hydroxide at a concentration above the solubility product of 0.03 M, a strontium salt deposit will be formed on the oxide surface (implant surface). This is also due to the excess of hydroxide groups in the surrounding.

However, the step of forming a deposit of e.g. a strontium salt is not limited to any specific method, but any method may be used. Neither is it limited to a specific strontium salt, but any salt which is at least partly soluble in the physiological fluid surrounding an implant may be used.

Furthermore, any method for forming a salt precipitation comprising any or a combination of the ions selected from strontium, lithium, magnesium and calcium can be used, e.g. the solution which comprises strontium may also comprise any or a combination of the above mentioned ions. In such cases, a small amount of these ions may also become incorporated into the oxide layer.

The step of forming a deposit may also be performed by a combination of the above mentioned methods.

It should however be noted that known methods for ion incorporation and deposit formation on an implant surface may also be used in the present invention. Such methods include e.g.:

plasma deposition, for instance using plasma source ion implantation or metal plasma immersion ion implantation, any electrochemical treatment, for instance voltametry in an electrolyte comprising strontium ions, treatment of the implant with an aqueous and/or non-aqueous solution comprising strontium ions, for instance by dipping said implant in said solution, treatment of the implant with a sol-gel technique, beam ion implantation, vacuum arc, filtered vacuum arc, metal vapour vacuum arc, ion plating, chemical vapour deposition, plasma assisted chemical vapour deposition, sputtering, laser ablation, providing a coating, such as a calcium phosphate-containing coating or a silane coating, on the implant surface, in or to which strontium ions can be incorporated or attached, any combination of these methods or the like.

The method according to the invention may further comprise the step of creating a micro roughness on the implant surface.

Before, simultaneously with and/or after the provision of strontium ions or a salt thereof on the implant surface, a nano- and/or micro-roughness can be optionally provided on the implant surface using, for instance, mild etching, microfabrication, anodization, flame spraying, electrochemical treatment, laser, spark erosion, or any other suitable method of surface modification. Reference can be made to WO 04/008983 and WO 04/008984, wherein suitable methods for obtaining such an implant surface are disclosed. It is however preferred that the nano- and/or micro-roughness is provided after step a) in the method according to the invention.

The method of the invention may also comprise the step of applying fluorine to the implant surface. Reference can be made to WO 04/008983, wherein suitable methods for obtaining such an implant surface are disclosed.

A suitable method, according to WO 04/008983, for providing fluorine and/or fluoride and a micro-roughness having a root-mean-square roughness ($R_q$ and/or $S_q$) of ≤250 nm on at least a part of an implant surface is by treatment of the implant with an aqueous solution of hydrofluoric acid having a concentration of less than 0.5 M, such as 0.1 M, for an etching period of up to 180 sec, such as 60 s, at room temperature (see WO 04/008983 for more information).

In addition, a macro-roughness can be optionally provided on the implant surface prior to providing strontium ions or a salt thereof, and prior to optionally providing the micro-roughness, thereon. A macro-roughness can, for instance, be provided by blasting, e.g. with titanium dioxide particles, etching, micro-fabrication, anodization, flame spraying, any electrochemical treatment, laser, spark erosion, machining, knurling, or any other suitable method of surface modification.

It shall also be noted that the implant surface may be either threaded or unthreaded or be given other use dependent topographical features.

The method for manufacturing a bone tissue implant according to the invention is not limited to the incorporation of strontium ions, but may be applied to incorporate positively charged ions into the implant surface in general. Hence, such a method involves the steps of:

a) providing an implant having an implant surface;
b) forming an oxide layer covering said implant surface;
c) forming negatively charged ions on said oxide layer; and
d) bringing said oxide layer into contact with positively charged ions.

The present invention further relates to a blasting powder, which comprises a metal oxide, wherein the metal oxide comprises strontium ions.

The metal oxide may be a metal oxide selected from the group consisting of titanium oxide, zirconium oxide, hafnium oxide, tantalum oxide, and niobium oxide. Preferably the blasting powder comprises titanium oxide into which strontium ions are incorporated.

It is also possible to simply use strontium oxide as the blasting powder of the present invention.

It may be possible to use said blasting powder in the method according to the invention to further enhance the incorporation of strontium ions into the oxide layer covering the implant surface. However, a blasting powder may be used by itself to incorporate strontium ions into any oxide layer provided on any implant surface.

The present invention also relates to a method for locally increasing bone formation. Such a method comprises administering a composition comprising strontium ions or a salt thereof and a pharmaceutically acceptable carrier to a person in need thereof. Preferably, the composition comprising strontium ions or a salt thereof and a pharmaceutically acceptable carrier is administered at an implantation site upon implantation of an implant into bone tissue at said implantation site before, simultaneously with and/or after said implant is placed in a cavity in the bone tissue at said site.

The composition comprising strontium ions, or a salt thereof, can be administered in and/or nearby said cavity in the bone tissue.

Examples of suitable pharmaceutically acceptable carriers for use in said composition are a physiological saline solution; disintegrated autologous bone; a demineralised bone matrix; liposomes; nano- or microparticles of biodegradable polymer(s), such as polylactic acid (PLA) and polyglycolic acid (PGA); hyaluronic acid; collagen; chondroitin sulfate; a hydrogel, such as alginate; chitosan; a scaffold of polyester and tricalcium phosphate; and the like.

A specific example of a suitable carrier is PepGen P-15 PUTTY™, which are particles of hydroxyapatite enhanced with P-15, a synthetic peptide that mimics the cell-binding region of Type-I collagen, suspended in sodium hyaluronate.

The composition according to the invention can either be an immediate release, a delayed release or a controlled release formulation.

The invention also relates to the use of strontium ions, or a salt thereof, for manufacturing a pharmaceutical composition (as disclosed above) for locally increasing bone formation.

The composition may be locally administered at an implantation site upon implantation of an implant into bone tissue at said site.

According to the present inventors, local administration of strontium ions or a salt thereof directly into the bone tissue is preferred over systemic administration. Foreign agents often have a variety of effects on the human body, which are both known and unknown. Local administration of strontium or a salt thereof in bone tissue is beneficial as the bone stimulating effect will be achieved, while side effects are avoided.

In addition, the invention relates to a kit for implantation of an implant into bone tissue comprising an implant and a composition (as disclosed above) comprising strontium ions, or a salt thereof, and a pharmaceutically acceptable carrier.

While the invention has been described in detail and with reference to specific embodiments thereof, it will be apparent for one skilled in the art that various changes and modifications can be made therein without departing from the spirit and scope thereof.

The invention will now be illustrated by means of the following non-limiting examples.

Example 1: Incorporation of Strontium Ions into a Titanium Oxide Layer

Reduction in $Sr(NO_3)_2$

Titanium samples were reduced by potential step technique in 0.1 M $Sr(NO_3)_2$, pH 5-6. A potential step of −3V (all potentials are referred to a double junction Ag/AgCl/KCl reference electrode, 197 mV against SHE) was applied over the sample for 5 minutes resulting in a continuous hydrogen evolution. After the reduction process the samples were rinsed in MQ water in an ultrasonic bath for 2 minutes before drying and sterilization.

The presence of strontium was identified by X-ray photoelectron spectroscopy analysis (XPS analysis). The results are presented in table 1 below.

TABLE 1

| XPS analysis of samples reduced in $Sr(NO_3)_2$ (the amounts are given in at %) | | | | | | | |
|---|---|---|---|---|---|---|---|
| Sample | Spec. | β-sterilized | C1s | N1s | O1s | Ti2p | Sr3d |
| 1 | Sr | no | 23.1 | 1.1 | 53.3 | 20.2 | 2.0 |
| 2 | Sr | no | 22.7 | 0.7 | 53.8 | 20.1 | 2.6 |
| 3 | Sr | yes | 22.1 | 1.2 | 54.4 | 20.8 | 1.5 |
| 4 | Sr | yes | 22.4 | 1.7 | 54.5 | 19.8 | 1.7 |

Soaking in $Sr(OH)_2$

Titanium samples were soaked in 0.1 M $Sr(OH)_2$, pH>11, at 40° C. for 10 minutes. After this the samples were rinsed in MQ water in an ultrasonic bath until the rinsing water reached a neutral pH value. The samples were dried and β-sterilized before analysis. The presence of strontium was identified by XPS-analysis.

TABLE 2

| XPS analysis of samples soaked in $Sr(OH)_2$ (the amounts are given in at %) | | | | | | | |
|---|---|---|---|---|---|---|---|
| Sample | Spec. | β-sterilized | C1s | N1s | O1s | Ti2p | Sr3d |
| 5 | Sr | no | 23.7 | 0.8 | 52.7 | 21.8 | 1.0 |
| 6 | Sr | no | 22.9 | 0.7 | 52.7 | 22.7 | 1.1 |
| 7 | Sr | yes | 23.1 | 0.7 | 53.2 | 22.1 | 0.9 |
| 8 | Sr | yes | 22.6 | 0.7 | 53.1 | 22.5 | 1.1 |

Anodizing in an Alkaline Solution

Titanium samples were anodized/oxidized in 0.1 M $Sr(OH)_2$, pH>11 by LSV (linear sweep voltammetry) from OC (open circuit) to 7V (all potentials are referred to a double junction Ag/AgCl/KCl reference electrode, 197 mV against SHE), at a scan rate of 2 and/or 5 mV/s and a rotation speed of 900 rpm. After the anodization process the samples were rinsed in MQ water in an ultrasonic bath for 2 minutes before drying and sterilization.

Figure 3:
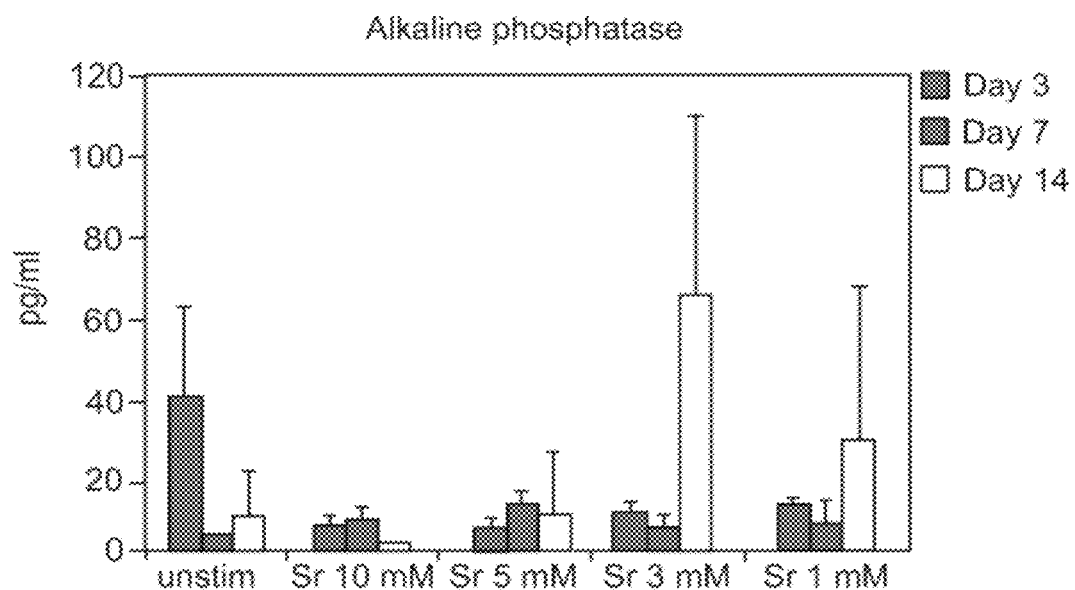
FIG. 3 illustrates the production of alkaline phosphatase in the cell culture medium after 3, 7 and 14 days of cell culture on cell treated polystyrene polystyrene with and without strontium in different concentrations.

The presence and distribution of strontium at the surface of the samples were identified using Time-of-Flight Secondary Ion Mass Spectrometry (TOF-SIMS) and the amount of strontium at the surface were analysed by XPS. The presence and the distribution of strontium ions are illustrated in FIGS. 2 and 3.

TABLE 3

XPS analysis of samples anodized in Sr(OH)$_2$ at a scan rate of 2 mV/s (the amounts are given in at %)

| Sample | Spec. | β-sterilized | C1s | O1s | Ti2p | Sr3d |
|---|---|---|---|---|---|---|
| 9 | Sr | no | 18.6 | 59.4 | 18.6 | 3.5 |
| 10 | Sr | no | 19.1 | 59.1 | 17.8 | 4.0 |
| 11 | Sr | yes | 31.3 | 51.6 | 15.0 | 2.1 |
| 12 | Sr | yes | 31.6 | 51.4 | 14.0 | 3.1 |

Example 2: Release of Strontium from a Titanium Implant Surface

Titanium samples were reduced by potential step technique in 0.1 M Sr(NO$_3$)$_2$, pH 5-6. A potential step of at least −4V (all potentials are referred to a double junction Ag/AgCl/KCl reference electrode, 197 mV against SHE) was applied over the sample for 5 minutes resulting in a vigorous hydrogen evolution. After the reduction process the samples were rinsed in MQ water and dried. The presence of strontium was identified by XPS-analysis.

TABLE 5

XPS analysis of samples reduced in Sr(NO$_3$)$_2$ at a potential more negative than −4 V (the amounts are given in at %)

| Sample | Spec. | β-sterilized | C1s | N1s | O1s | Ti2p | Sr3d |
|---|---|---|---|---|---|---|---|
| 13 | Sr | no | 22.7 | 0.8 | 53.5 | 20.9 | 2.1 |
| 14 | Sr | no | 22.9 | 0.8 | 53.5 | 21.2 | 1.7 |
| 15 | Sr | yes | 23.1 | 1.5 | 52.7 | 20.7 | 2.0 |
| 16 | Sr | yes | 21.4 | 1.4 | 54.4 | 21.1 | 1.8 |

The release of strontium was identified by ICP (Inductivly Coupled Plasma). Four coin shaped samples, prepared according to the above, were placed in a beaker with 15 ml MQ water. The water was acidified to pH 4 using 20 mM HNO$_3$ and thereafter left for 90 minutes during moderate agitation before analysis. The solution was analysed using ICP giving the result of 50 μg strontium/ml sample.

Reference Example 1: Culturing of MG-63 Cells

MG-63 is a human cell line (ATCC No CRL-1427, U.S.) conventionally used in the art for in vitro studies of osteoblasts. MG-63 origins from a human osteosarcoma and exhibits numerous trait characteristics of human osteoblasts, such as alkaline phosphatase (ALP), prostaglandin E2 (PGE2) and osteoprotegerin (OPG).

In this study, MG-63 cells were obtained from frozen cells in second passage and further cultured in Dulbecco's modified Eagle's medium (DMEM) containing FCS 5%, PEST 1%, Gibco, UK) in 37° C. in an atmosphere of 5% CO$_2$ and 100% humidity. When the cells reached confluence they were subcultured by the use of 0.05% Trypsin-EDTA (Gibco, UK) until the amount of cells were obtained.

Cell viability was high in all experiments (>98%) and was checked by the use of trypan blue where the uptake of the stain by dead cells was checked in a Bürkerchamber in a light microscope (LM).

Reference Example 2: Production of Alkaline Phosphatase (ALP)

In order to study the effect of strontium on the production of alkaline phosphatase (ALP), MG-63 cells prepared in reference example 1 were subcultured into 24 well plates at a plating density of 10 000 cells/cm$^2$, in total 20 000 cells/well. Sterile filtered Sr(NO$_3$)$_2$ at final concentrations of 10 mM, 5 mM, 3 mM, and 1 mM respectively (pH 5.2) were added to the respective wells of the plate. Untreated cells were used as controls. Cells were cultured for 3, 7 and 14 days at a temperature of 37° C. in an atmosphere of 5% CO$_2$ and 100% humidity.

At harvest, the cell culture medium was analysed with respect to the ALP content. The intracellular ALP was measured by cell lysis according to the instructions of the manufacturer (SenzoLyte™ pNPP Alkaline Phosphatase Assay Kit Colorimetric BioSite, Sweden). The absorption was set at 405 nm by an automatic plate reader (Vmax, Molecular Device, UK). By comparing the optical density of the samples with the standard provided with the kit, the ALP concentrations could be determined. The instructions from the manufacturer were followed (BioSite, Sweden).

The production of ALP was initially slow with all strontium concentrations compared to control (unstimulated cells). A small increase was detected after 7 days. However, remarkably increased ALP levels were observed after 14 days, especially at the Sr concentrations 1 mM and 3 mM. The highest amount of ALP was obtained with 3 mM strontium after 14 days of culturing. The results are illustrated in FIG. 3.

Reference Example 3: Preparation of Reference Surfaces

Titanium samples having the shape of a coin were cleaned, and then immersed in an 1 M aqueous solution of oxalic acid and left at 80° C. for 30 minutes under vigorous agitation. After 30 minutes the samples were removed from the oxalic acid solution and rinsed in MQ water followed by rinsing in MQ water in an ultrasonic bath for 2 minutes. The resulting surface is referred to as "reference surface 1".

Some of the samples were subjected to a secondary hydrofluoric acid treatment. Approximately 10 minutes after rinsing, the samples were immersed in 0.1 M aqueous solution of HF at room temperature and agitation until the start of active dissolution, followed by an additional active treatment time of 40 s. Next, the samples were removed from the HF solution and rinsed in MQ water followed by rinsing in MQ water in an ultrasonic bath for 2 minutes. The samples were dried in air at room temperature for about 60 minutes before sterilization. The resulting surface is referred to as "reference surface 2"

Reference Example 4: MG-63 Proliferation on Reference Surfaces

Sterilized (β-radiation) Ti coins with reference surfaces 1 and 2, respectively were placed in 24 well plates. MG-63 cells were subcultured onto the coins in the 24 well plates at a plating density of 10 000 cells/cm$^2$, in total 20 000 cells/well. Sterile filtered Sr(NO$_3$)$_2$ at final concentrations of 5 mM and 0.5 mM (pH 5.2) was added to the respective wells. Untreated cells were used as controls. Cells were cultured for 7 days at a temperature of 37° C. in an atmosphere of 5% CO$_2$ and 100% humidity.

The total number of cells in each well ($\times 10^5$) after each time period was determined by the NucleoCassette method by the NucleoCounter (ChemoMetec A/S Denmark).

The number of cells was investigated by lysis of the cells in "Reagent A" having a pH of 1.25 following stabilization by "Reagent B". In the NucleoCassette, propidium iodide was incorporated which targets the amount of released DNA. The cassette was placed in the NucleoCounter and the amount of measured fluorochrome corresponded to the amount of DNA. The instructions from the manufacturer were followed (Chemometec A/S, Denmark).

Figure 4:
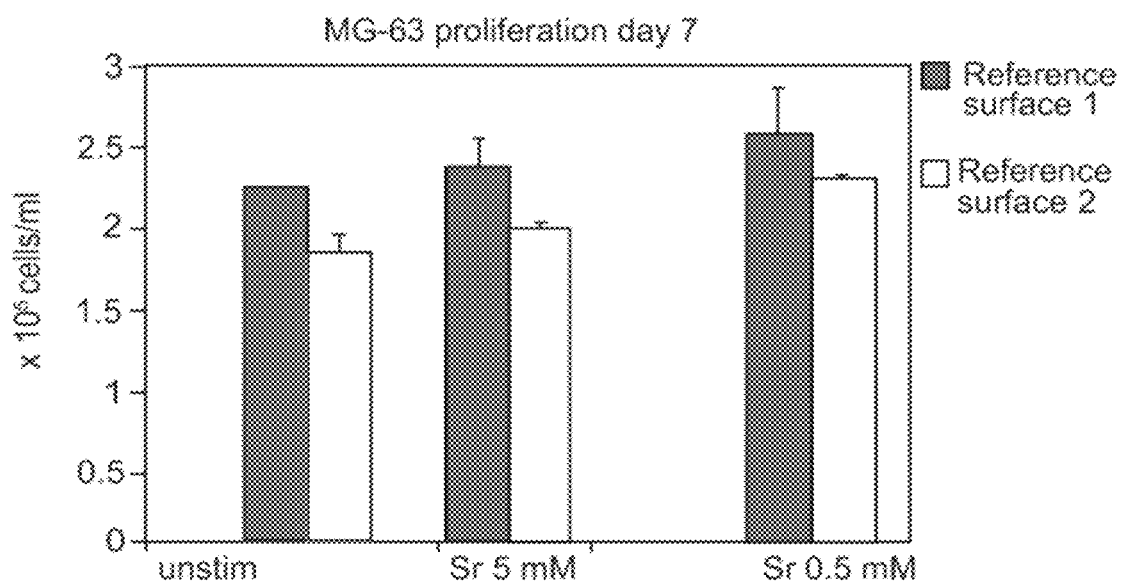
FIG. 4 shows the degree of proliferation of MG-63 cells on reference surface 1 comprising 0.5 mM and 5 mM strontium compared to unstimulated reference surfaces 1 and 2 after 7 days of culture.

Referring to FIG. 4, the reference surfaces comprising strontium induced an increased proliferation of MG-63 cells after 7 days of culture. Strontium at a concentration of 0.5 mM induced the highest MG-63 cell proliferation compared to the unstimulated reference surfaces 1 and 2.

Reference Example 5: ALP Production on Reference Surfaces

The production of ALP on reference surface 1 comprising a concentration of 0.5 mM strontium was compared with unstimulated reference surfaces 1 and 2.

Figure 5:
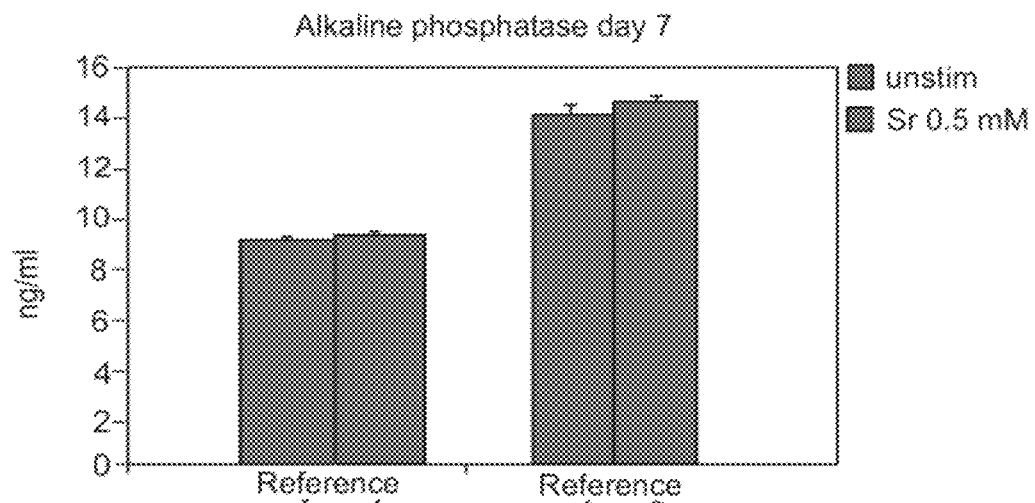
FIG. 5 shows the production of alkaline phosphatase on reference surface 1 comprising strontium at a concentration of 0.5 mM compared to unstimulated reference surfaces 1 and 2.

As is illustrated in FIG. 5, an increased production of ALP was observed with 0.5 mM strontium after 7 days of cell culture.

Reference Example 6: Production of Prostaglandin E2 (PGE2)

The production of PGE2 after 7 and 14 days was analyzed using titanium samples with reference surface 1 comprising strontium. The results were compared to unstimulated reference surfaces 1 and 2.

To obtain the quantitative assessment of Prostaglandin E2 (PGE2) an ELISA method from R&D Systems PGE2 Immunoassay (R&D Systems, UK) was used. The supernatant from each well was centrifuged free of cells (5 min in 400 g) and further used for investigation. Sample PGE2 concentrations were determined by correlating the amounts to the standard curve provided by the manufacturer. The sensitivity of the test (MDD, minimum detectable dose) was 27.5 pg/ml. The instructions from the manufacturer were followed (R&D Systems, UK).

Figure 6:
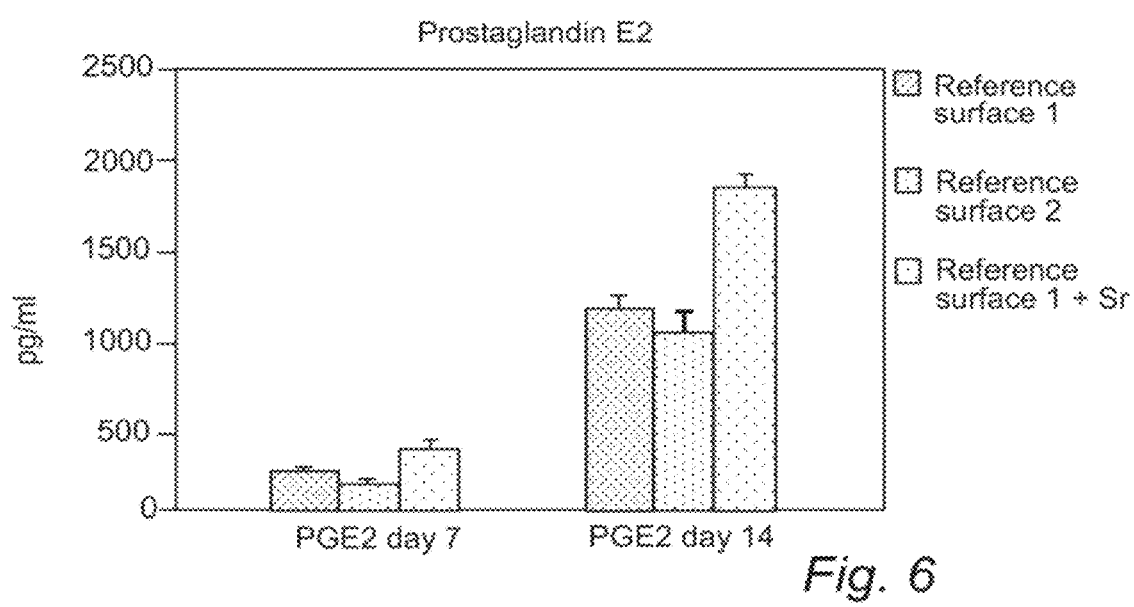
FIG. 6 illustrates the amount of prostaglandin E2 (PGE2) measured after 7 and 14 days of cell culture on reference surface 1 comprising strontium compared to unstimulated reference surfaces 1 and 2.

After 7 days an increased PGE2 production could be observed with the reference surface 1 comprising strontium compared to the unstimulated reference surfaces. The PGE2 production was further increased after 14 days of culture. The results are illustrated in FIG. 6.

Reference Example 7: Morphology

Titanium samples having (i) reference surface 1 (ii) reference surface 2, and (iii) reference surface 1+strontium were prepared for Scanning Electron Microscopy (SEM). The samples were fixated by glutaraldehyd i+4° C. (Kanowsky's), followed by osmium tetroxid, dehydration and finally gold sputtered according to the standard techniques.

Figure 7:
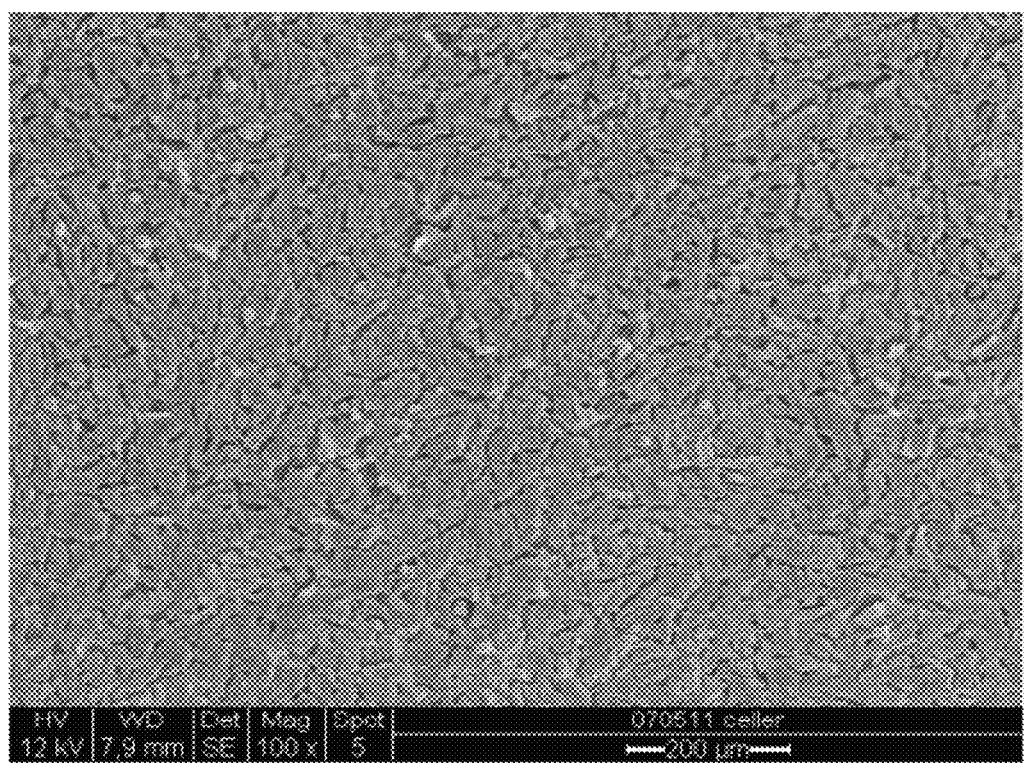
FIG. 7 is a scanning electron microscopy image illustrating the morphology of MG-63 cells cultured on reference surface 1 after 36 h.
Figure 8:
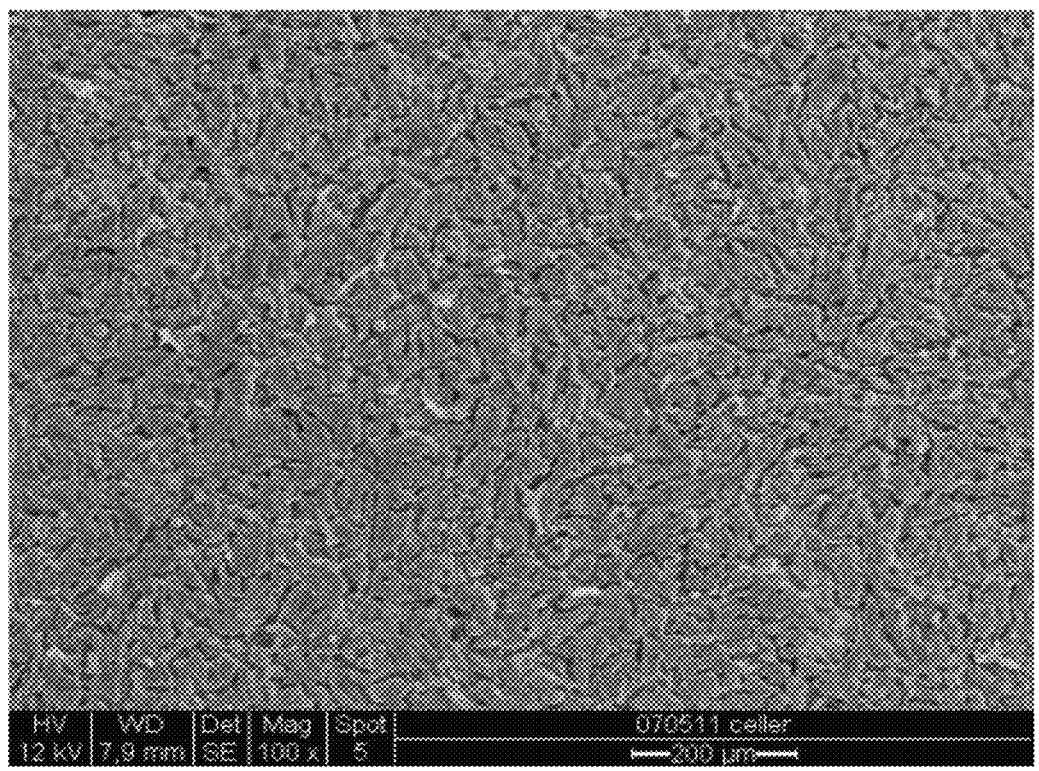
FIG. 8 is a scanning electron microscopy image illustrating the morphology of MG-63 cells cultured on reference surface 2 after 36 h.
Figure 9:
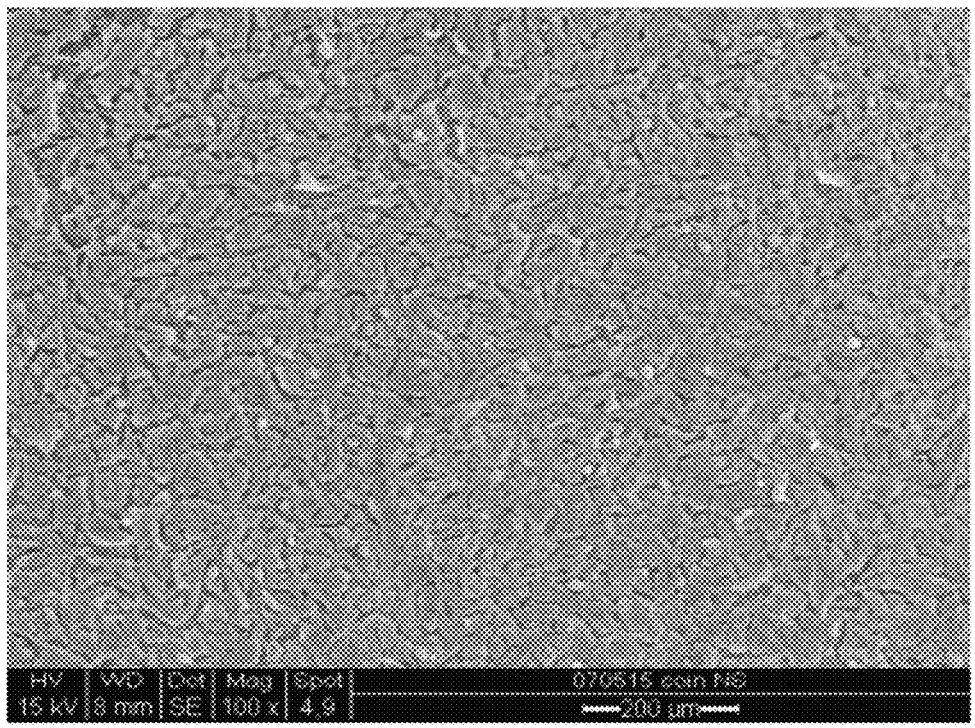
FIG. 9 is a scanning electron microscopy image illustrating the morphology of MG-63 cells cultured on reference surface 1 comprising strontium after 36 h.

The FIGS. 7, 8, and 9 illustrate the morphology of the respective surface after 36 h. The reference surface 1 comprising strontium has a larger amount of cells in proliferative stage (FIG. 9) (round, non-spread cells) as well as a large amount of adhesive cells compared to cells on unstimulated reference surfaces 1 and 2. On both the reference surface 1 (FIG. 7) and reference surface 2 (FIG. 8) the cells are thinner, flatter and more spread out.

The space between the cells on the reference surfaces 1 and 2 is probably due to fixation difficulties and is often seen when cells are very thin and spread out.

The morphology of the cells cultured on the reference surface 1 comprising strontium shows that the cells are well spread out, indicating high activity, proliferate, and form matrix and pseudopodia on the surfaces. This indicates that such surfaces are osteoconductive as well as osteoinductive and in favor for cell adhesion, proliferation and matrix formation.

Comparative Example 1: MG-63 Proliferation on Reference Surfaces Comprising Strontium, Calcium and Magnesium, Respectively Sterilized (($\beta$ radiation) Ti coins with reference surfaces 1 and 2 were compared with Ti coins having reference surface 1 comprising strontium, calcium and magnesium, respectively, and the coins were placed in 24 well plates. MG-63 cells were subcultured onto the coins in the 24 well plates at a plating density of 10 000 cells/cm$^2$, in total 20 000 cells/well. Cells were cultured for 7 days at a temperature of 37° C. in an atmosphere of 5% $CO_2$ and 100% humidity.

The total number of cells in each well ($\times 10^5$) after each time period was determined by the NucleoCassette method by the NucleoCounter (ChemoMetec A/S Denmark).

The number of cells was investigated by lysis of the cells in "Reagent A" having a pH of 1.25 following stabilization by "Reagent B". In the NucleoCassette, propidium iodide was incorporated which targeted the amount of released DNA. The cassette was placed in the NucleoCounter and the amount of measured fluorochrome corresponded to the amount of DNA. The instructions from the manufacturer were followed (Chemometec A/S, Denmark).

Figure 10:
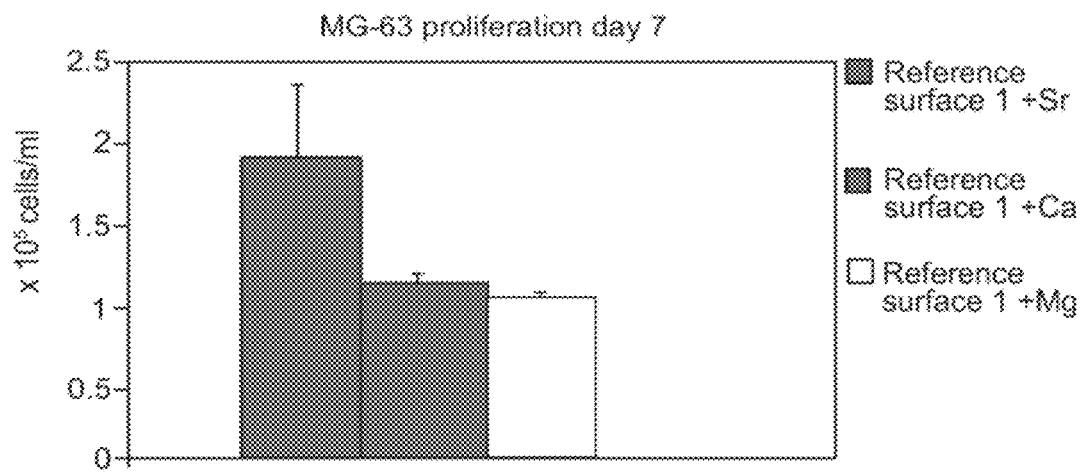
FIG. 10 illustrates the differences in MG-63 cell proliferation between reference surface 1 comprising strontium, calcium and magnesium, respectively.

Referring to FIG. 10, the reference surface 1 comprising strontium showed the highest MG-63 cell proliferation after 7 days of cell culture. The cell proliferation was markedly higher than for the reference surface 1 comprising calcium and magnesium.

Comparative Example 2: Production of Osteoprotegerin on Reference Surface 1 Comprising Strontium, Calcium and Magnesium, Respectively The production of osteoprotegerin (OPG) after 7 and 14 days was compared between Ti coins with reference surface 1 comprising strontium, calcium and magnesium, respectively.

The amount OPG was determined by DuoSet ELISA human OPG/TNFRSF11B (R&D Systems, UK). The supernatant from each well was centrifuged free of cells (5 min in 400 g) and further used for investigation. Sample OPG concentrations were determined by correlating the amounts to the standard curve provided by the manufacturer. The sensitivity of the test (MDD, minimum detectable dose) was 50 pg/ml. The instructions from the manufacturer were followed (R&D Systems, UK).

Figure 11:
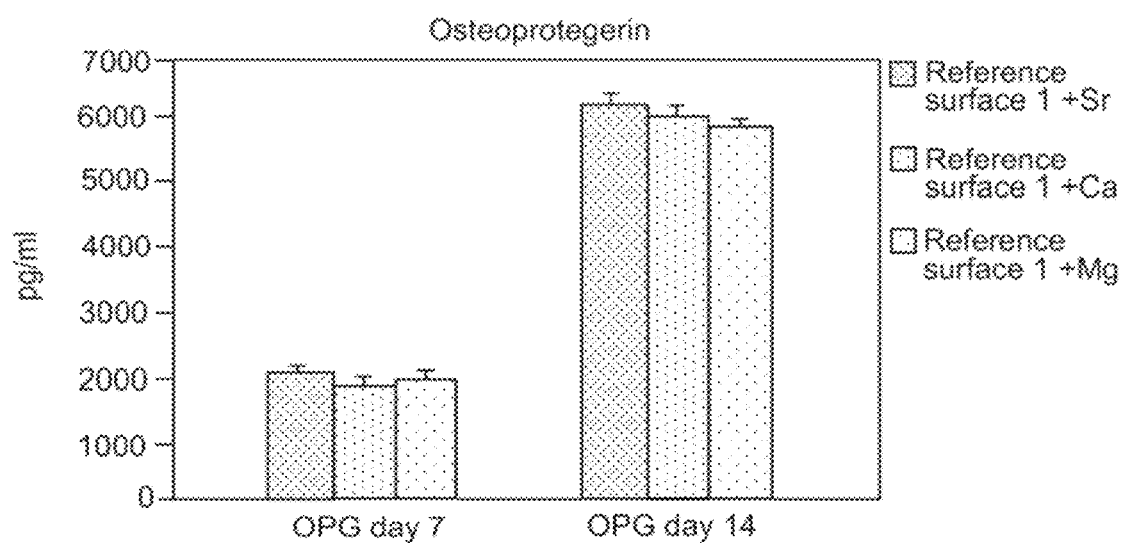
FIG. 11 shows the amount of osteoprotegerin measured after 7 and 14 days of cell culture on reference surface 1 comprising strontium, calcium, and magnesium, respectively.

As is illustrated in FIG. 11, the highest production of OPG was observed with the reference surface 1 comprising strontium, both after 7 and 14 days of cell culture.

Comparative Example 3: Bone Tissue Response in Vivo

Integration of implants according to the invention was tested in a rabbit model. The objective was to qualitatively and quantitatively study the in vivo bone tissue response of implant surface modifications according to the invention compared to commercially available control implants.

Implants for Removal Torque Study

Torque fixtures (square headed removal torque design, 3.5×8.2 mm) with reference surface 1 comprising strontium were compared with two control fixtures: (1) torque fixtures (3.5×8.2 mm) with reference surface 1 (without strontium) and (2) torque fixtures (3.5×8.2 mm) with the commercially available Osseospeed™ surface.

Implant Insertion

Twelve mature male New Zealand white rabbits were scheduled for surgery. Two rabbits died during initial anaesthesia (#9, 10). The surgery went uneventful. Low speed drilling (1500 rpg for drilling the holes and 20 rpm for implant insertion) was done with continuous NaCl cooling. The first drill was a small round burr and thus used as a marker for the coming larger spiral drills (altogether 6 drills having diameters in the range of from 1.2 to 3.35 mm).

Three implants ("square headed removal torque design"; 3.5×8.2 mm) were inserted in each tuburositas tibia. The tibia implants were scheduled for removal torque tests.

Removal Torque Results

After six weeks the study was terminated and the rabbits were sacrificed. The implants and surrounding tissue were examined. The tibia rtq implants were easy to locate and all of them showed signs of periosteal bone tissue up-growth. The biomechanical test of the implant-bone interface was performed with the removal torque test (RTQ). The RTQ instrument is an electronic equipment (Detektor Aft Göteborg, Sweden) involving a strain gauge transducer used for testing the implant stability (the peak loosening torque in Ncm) in the bone bed and can thus be regarded as a three dimensional test roughly reflecting the interfacial shear strength between bone tissue and the implant (Johansson C. B., Albrektsson T. *Clin Oral implants Res* 1991; 2:24-9). A linear increasing torque was applied on the same axis of the implant until failure of integration was obtained and the peak value was noted.

As is illustrated in FIG. 12, the removal torque value for the implant comprising strontium according to the invention was significantly improved compared to both the control surfaces lacking strontium.

The invention claimed is:

1. A method for manufacturing a bone tissue implant having an implant surface covered by a metal oxide layer comprising strontium ions, said method comprising the steps of:
    a) providing an implant having an implant surface covered by a native metal oxide layer;
    b) forming negative charges on the native metal oxide layer by applying a potential of −0.5 V or less to generate surface bound negatively charged hydroxide groups, creating locally alkaline sites on the surface; and
    c) bringing said native metal oxide layer into contact with an aqueous solution comprising strontium ions, thereby forming a metal oxide layer having a thickness within the range of from 2 to 100 nm and having strontium ions homogenously incorporated therein;
    wherein said step b and said step c are performed simultaneously.

2. A method according to claim 1, wherein said metal oxide layer is formed spontaneously.

3. A method according to claim 1, wherein negatively charged ions on said native metal oxide layer are formed by applying the potential within the range of −0.5 V to −3.5 V.

4. A method according to claim 1, wherein said aqueous solution comprises strontium hydroxide.

5. A method according to claim 4, wherein said aqueous solution comprises strontium hydroxide in a concentration of 0.03 M or less.

6. A method according to claim 1, further comprising the step of forming a deposit comprising a bone stimulating agent on top of said metal oxide layer.

7. A method according to claim 6, wherein said bone stimulating agent is selected from the group consisting of strontium, lithium, calcium and magnesium or a combination thereof.

8. A method according to claim 6, wherein said deposit is formed by precipitating a salt comprising any one or a combination of the ions selected from the group consisting of strontium, lithium, calcium and magnesium on said metal oxide layer.

9. A method according to claim 8, wherein said salt is strontium hydroxide.

10. A method according to claim 8, wherein said deposit is formed by applying a potential which is more negative than −3.5 V.

11. A method according to claim 9, wherein said deposit is formed by subjecting said implant surface to an alkaline solution comprising strontium hydroxide in a concentration of more than 0.03 M.

12. A method according to claim 1, further comprising the step of creating a micro roughness on said surface of said implant after step a).

13. A method according to claim 1, further comprising the step of applying fluorine to said surface of said implant.

14. A method according to claim 1, wherein said implant is a metallic implant.

15. A method according to claim 14, wherein said metallic implant comprises titanium or an alloy of titanium.

16. A method according to claim 1, wherein said implant is a non-metallic implant; said surface being an applied metallic implant layer.

17. A method according to claim 16, wherein said metallic implant layer comprises titanium or an alloy of titanium.

18. A method according to claim 1, wherein said metal oxide layer has a thickness within the range of from 2 to 18 nm.

19. A method according to claim 1, wherein said metal oxide layer has a thickness within the range of from 2 to 6 nm.

20. A method according to claim 1, wherein said metal oxide layer is a metal oxide layer formed from said surface of said implant.

21. The method according to claim 1, wherein said metal oxide layer is formed spontaneously, and said metal oxide layer has a thickness within the range of from 2 to 18 nm.

22. The method according to claim 21, further comprising the step of d) rinsing and/or cleansing said implant surface after the simultaneous performance of step b and step c.

23. The method according to claim 1, further comprising the step of d) rinsing and/or cleansing said implant surface after the simultaneous performance of step b and step c.

\* \* \* \* \*